(12) United States Patent
Brady et al.

(10) Patent No.: US 8,323,616 B2
(45) Date of Patent: Dec. 4, 2012

(54) SOLID-PHASE FLUORINATION OF BENZOTHIAZOLES

(75) Inventors: Frank Brady, London (GB); Sajinder Kaur Luthra, London (GB); Alexander Mark Gibson, Amersham (GB)

(73) Assignees: GE Healthcare Limited, Amersham (GB); Hammersmith Imanet Limited, London (GB)

( * ) Notice: Subject to any disclaimer, the term of this patent is extended or adjusted under 35 U.S.C. 154(b) by 1323 days.

(21) Appl. No.: 10/539,169

(22) PCT Filed: Dec. 19, 2003

(86) PCT No.: PCT/GB03/05574
§ 371 (c)(1), (2), (4) Date: Jun. 14, 2005

(87) PCT Pub. No.: WO2004/056399
PCT Pub. Date: Jul. 8, 2004

(65) Prior Publication Data
US 2006/0083677 A1    Apr. 20, 2006

(30) Foreign Application Priority Data
Dec. 20, 2002  (GB) .................................. 0229686.1

(51) Int. Cl.
*A61K 51/00*  (2006.01)
*A61M 36/14*  (2006.01)
(52) U.S. Cl. ..................................... 424/1.65; 424/1.89
(58) Field of Classification Search .......................... None
See application file for complete search history.

(56) References Cited

U.S. PATENT DOCUMENTS

| | | | |
|---|---|---|---|
| 4,540,648 A | 9/1985 | Scheler | |
| 5,312,592 A | 5/1994 | Andersson | |
| 2004/0236085 A1* | 11/2004 | Luthra et al. | 536/1.11 |

FOREIGN PATENT DOCUMENTS

| | | |
|---|---|---|
| WO | 97/42203 | 11/1997 |
| WO | 99/18053 | 4/1999 |
| WO | 01/14354 | 3/2001 |
| WO | 03/068269 | 8/2001 |
| WO | 02/16333 | 2/2002 |
| WO | 02/070020 | 9/2002 |
| WO | 03/002157 | 1/2003 |
| WO | 03/002489 | 1/2003 |

OTHER PUBLICATIONS

Shuttleworth et al. (Synthesis 1997, 1217-1239).*
Sutliffe-Goulden, et.al.: "Solid Phase Synthesis of F-Labelled peptides for Positron emission Tomography" Bioorganic & Medicinal Chemistry Letters, Oxford, GB vol. 10, No. 14 Jul. 17, 2000 pp. 1501-1503.
Labroo V.M. et.al.: "Direct Electrophilic Fluorination of Tyrosine in Dermorphin Analogues and its Effect on Biological Activity Receptor Affinity and Selectivity" Int'l Journal of Peptide & Protein Research, vol. 37, No. 5, 1991, pp. 430-439.
Chemical Abstract AN 1988:130967 of J. of Labelled Compounds and Radiopharm (1987), vol. 24(9), pp. 1029-1042.
International Search Report for PCT/GB/03/05574 dated Apr. 2004.
International Preliminary Examination Report for PCT/GB03/05574.
GB Search Report for GB0229686.1 dated May 2003.
Shah, et.al. The synthesis of 18F fluoroarenes from the reaction of cyclotron-produced 18F, fluoride ion with diaryliodonium salts, and J. Chem. Soc . Perkin Trans . Year 1998, 1, 2043-2046.

* cited by examiner

*Primary Examiner* — Michael G Hartley
*Assistant Examiner* — Melissa Perreira

(57) ABSTRACT

The invention provides a process for the production of an $^{18}$F-labelled tracer which comprises treatment of a solid support-bound precursor of formula (I) SOLID SUPPORT-LINKER-X-TRACER (I) wherein X is a group which promotes nucleophilic substitution at a specific site on the attached TRACER and the TRACER is of formula (A).

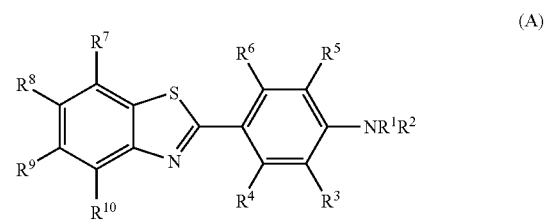

2 Claims, No Drawings

SOLID-PHASE FLUORINATION OF BENZOTHIAZOLES

This application is a filing under 35 U.S.C. 371 of international application number PCT/GB2003/005574, filed Dec. 19, 2003, which claims priority to application number 0229686.1 filed Dec. 20, 2002, in Great Britain the entire disclosure of which is hereby incorporated by reference.

The present invention relates to novel solid-phase processes for the production of radiolabelled tracers, in particular for the production of $^{18}$F-labelled benzothiazole compounds which may be suitable for use as Positron Emission Tomography (PET) radiotracers. The invention also comprises radiopharmaceutical kits using these novel processes.

The favoured radioisotope for PET, $^{18}$F, has a relatively short half-life of 110 minutes. $^{18}$F-labelled tracers for PET therefore have to be synthesised and purified as rapidly as possible, and ideally within one hour of clinical use. Standard synthetic methods for introducing fluorine—18 are relatively slow and require post-reaction purification (for example, by HPLC) which means that it is difficult to obtain the $^{18}$F-labelled tracer for clinical use in good radiochemical yield. There is also a need for automation to protect the operator from radiation exposure. Many radiofluorinations are complicated procedures and it is necessary to simplify them to facilitate automation.

The present invention provides solid-phase processes for producing $^{18}$F-labelled tracers quickly and with high specific activity yet avoiding time-consuming purification steps, such that the resultant $^{18}$F-labelled tracer is suitable for use in PET. The solid-phase methods also lend themselves to automation with advantages of ease of production and greater throughput. The invention also comprises radiopharmaceutical kits which use such processes and thus provide the radiopharmacist or clinician with a convenient means of preparing an $^{18}$F-labelled tracer.

Various substituted benzothiazole compounds, having utility for in vivo imaging of Alzheimer's Disease have been described in WO02116333. Solid-phase nucleophilic fluorination methods are described in co-pending International Patent Application PCT/GB02/02505.

In a general aspect, the invention provides a process for the production of an $^{18}$F-labelled tracer which comprises treatment of a solid support-bound precursor of formula (I)

SOLID SUPPORT-LINKER-X-TRACER    (I)

wherein the TRACER is of formula (A)

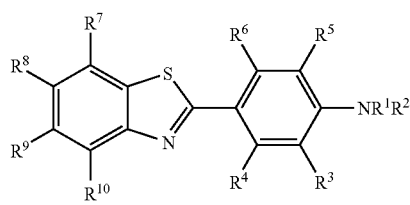

(A)

wherein:
R$^1$ and R$^2$ are independently selected from hydrogen, a protecting group, C$_{1-6}$ alkyl, C$_{1-6}$ hydroxyalkyl, and C$_{1-6}$ haloalkyl;
R$^3$ to R$^{10}$ are independently selected from hydrogen, halo, C$_{1-6}$ alkyl, C$_{1-6}$ haloalkyl, C$_{1-6}$ hydroxyalkyl, C$_{1-6}$ alkoxy, C$_{1-6}$ haloalkoxy, hydroxy, cyano, and nitro;

and one of the groups R$^1$ to R$^{10}$ is bonded to the SOLID SUPPORT-LINKER-X-;
with $^{18}$F$^-$ to produce the labelled tracer of formula (II)

$^{18}$F-TRACER    (II)

wherein the TRACER is as defined for the compound of formula (I) except that one of the groups R$^1$ to R$^{10}$ is bonded to the $^{18}$F instead of to the SOLID SUPPORT-LINKER-X- in formula (I);
optionally followed by:
(i) removal of excess $^{18}$F$^-$, for example by ion-exchange chromatography; and/or
(ii) removal of any protecting groups; and/or
(iii) removal of organic solvent; and/or
(iv) formulation of the resultant compound of formula (II) as an aqueous solution.

As the $^{18}$F-labelled tracer of formula (II) is removed from the solid-phase into solution, all unreacted precursor remains bound to the resin and can be separated by simple filtration, thus obviating the need for complicated purification, for example by HPLC. The $^{18}$F-labelled tracer of formula (II) may be cleaned up by removal of excess F$^-$, for example by ion-exchange chromatography and/or by removal of any organic solvent. The resultant $^{18}$F-labelled tracer of formula (II) may then be further made-up into an aqueous formulation for clinical use.

In the compounds of formula (I), X is a group which promotes nucleophilic substitution at a specific site on the attached TRACER. Examples of X include—SO$_2$O— as in formula (Ia) below, and I$^+$ as in formula (Ib) below.

In a further aspect, the invention provides a process for the production of an $^{18}$F-labelled tracer which comprises treatment of a solid support-bound precursor of formula (Ia):

SOLID SUPPORT-LINKER-SO$_2$—O-TRACER    (Ia)

wherein the TRACER is of formula (Aa)

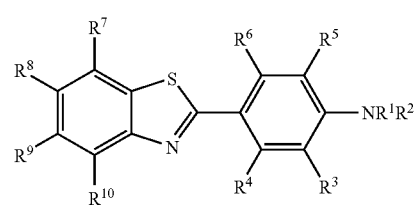

(Aa)

wherein:
R$^1$ and R$^2$ are independently selected from hydrogen, a protecting group, C$_{1-6}$ alkyl, C$_{1-6}$ hydroxyalkyl, and C$_{1-6}$ haloalkyl;
R$^3$ to R$^{10}$ are independently selected from hydrogen, halo, C$_{1-6}$ alkyl, C$_{1-6}$ haloalkyl, C$_{1-6}$ hydroxyalkyl, C$_{1-6}$ alkoxy, C$_{1-6}$ haloalkoxy, hydroxy, cyano, and nitro;
in which either (a) an R$^1$ C$_{1-6}$ alkyl group or (b) an R$^3$ to R$^{10}$ C$_{1-6}$ alkyl or C$_{1-6}$ alkoxy group is bonded to the SOLID SUPPORT-LINKER-SO$_2$—O— in formula (Ia);
with $^{18}$F$^-$ to produce the labelled tracer of formula (IIa)

$^{18}$F-TRACER    (IIa)

wherein the TRACER is as defined for the compound of formula (Ia) except that either (a) an R$^1$ C$_{1-6}$ alkyl group or (b) an R$^3$ to R$^{10}$ C$_{1-6}$ alkyl or C$_{1-6}$ alkoxy group is bonded to the $^{18}$F instead of to the SOLID SUPPORT-LINKER-SO$_2$—O— in formula (Ia);

optionally followed by:

(i) removal of excess $^{18}F^-$, for example by ion-exchange chromatography; and/or (ii) removal of any protecting groups; and/or (iii) removal of organic solvent; and/or (iv) formulation of the resultant compound of formula (IIa) as an aqueous solution.

In the compound of formula (Ia), the TRACER is suitably of formula (Aa1)

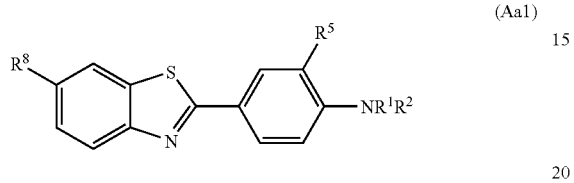

(Aa1)

wherein $R^1$ and $R^2$ are independently selected from hydrogen, a protecting group, $C_{1-6}$ alkyl, $C_{1-6}$ hydroxyalkyl, and $C_{1-6}$ haloalkyl;

$R^5$ is hydrogen or $C_{1-6}$ alkyl, $R^8$ is hydroxy, $C_{1-6}$ alkoxy, $C_{1-6}$ haloalkyl, or $C_{1-6}$ alkyl;

provided that one of $R^1$, $R^5$ and $R^8$ is $C_{1-6}$ alkyl bonded to the SOLID SUPPORT-LINKER-SO$_2$—O— in formula (Ia) or $R^8$ is $C_{1-6}$ alkoxy bonded to the SOLID SUPPORT-LINKER-SO$_2$—O— in formula (Ia).

As shown in Scheme 1, the compound of formula (Ia) may be conveniently prepared from any sulphonic acid functionalised commercially available resin, such as Merrifield Resin, NovaSyn® TG Bromo Resin, (Bromomethyl)phenoxymethyl polystyrene, or Wang Resin which may be reacted with a chlorinating agent to give the corresponding sulphonyl chloride resin. This may be carried out by treating the resin with, for example, phosphorus pentachloride, phosphorus trichloride, oxalyl chloride, or thionyl chloride, in an appropriate inert solvent such as dichloromethane, chloroform, or acetonitrile, and heating at elevated temperature for a period of time. The excess reagent may then be removed from the resin by washing with further portions of the inert solvent. The sulphonyl chloride resin may then be reacted with the alcohol analogue of the tracer to produce the resin-bound precursor of formula (Ia). This may be carried out by treating the resin with a solution of the alcohol in an inert solvent such as chloroform, dichloromethane, acetonitrile, or tetrahydrofuran containing a non-nucleophilic soluble base such as sodium hydride or a trialkylamine, for example triethylamine or diisopropylethylamine. The reaction may be carried out at a temperature of 10 to 80° C., optimally at ambient temperature for a period of from around 1 to 24 hours. The excess alcohol and base may then be removed from the solid support by washing with further portions of an inert solvent such as chloroform, dichloromethane, or tetrahydrofuran. Alternatively, the LINKER may be attached to the TRACER, before being attached to the SOLID SUPPORT to form the compound of formula (Ia), using analogous chemistry to that described above.

Scheme 1

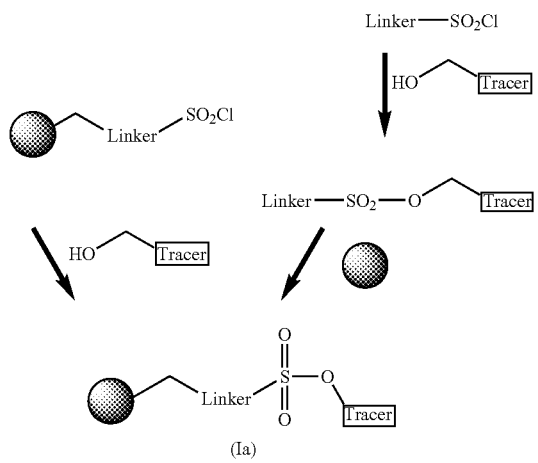

In the compounds of formulae (I) and (Ia) and in the following aspects of the invention, the "SOLID SUPPORT" may be any suitable solid-phase support which is insoluble in any solvents to be used in the process but to which the LINKER and/or TRACER can be covalently bound. Examples of suitable SOLID SUPPORT include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

In the compounds of formulae (I) and (Ia) and in the following aspects of the invention, the "LINKER" may be any suitable organic group which serves to space the reactive site sufficiently from the solid support structure so as to maximise reactivity. Suitably, the LINKER comprises zero to four aryl groups (suitably phenyl) and/or a $C_{1-16}$alkyl (suitably $C_{1-6}$alkyl) or $C_{1-16}$haloalkyl (suitably $C_{1-6}$haloalkyl), typically $C_{1-16}$ fluoroalkyl (suitably $C_{1-6}$ fluoroalkyl), or $C_{1-16}$alkoxy or $C_{1-6}$haloalkoxy (suitably $C_{1-6}$alkoxy or $C_{1-6}$haloalkoxy) typically $C_{1-16}$fluoroalkoxy (suitably $C_{1-6}$fluoroalkoxy), and optionally one to four additional functional groups such as amide or sulphonamide groups. Examples of such linkers are well known to those skilled in the art of solid-phase chemistry, but include:

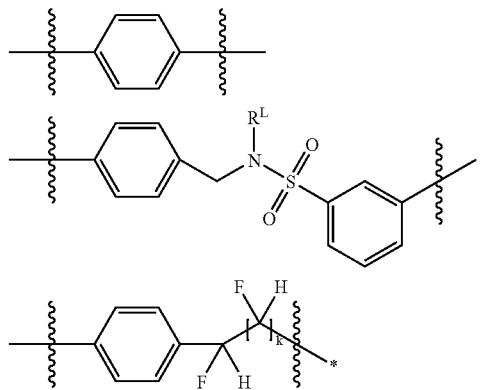

-continued

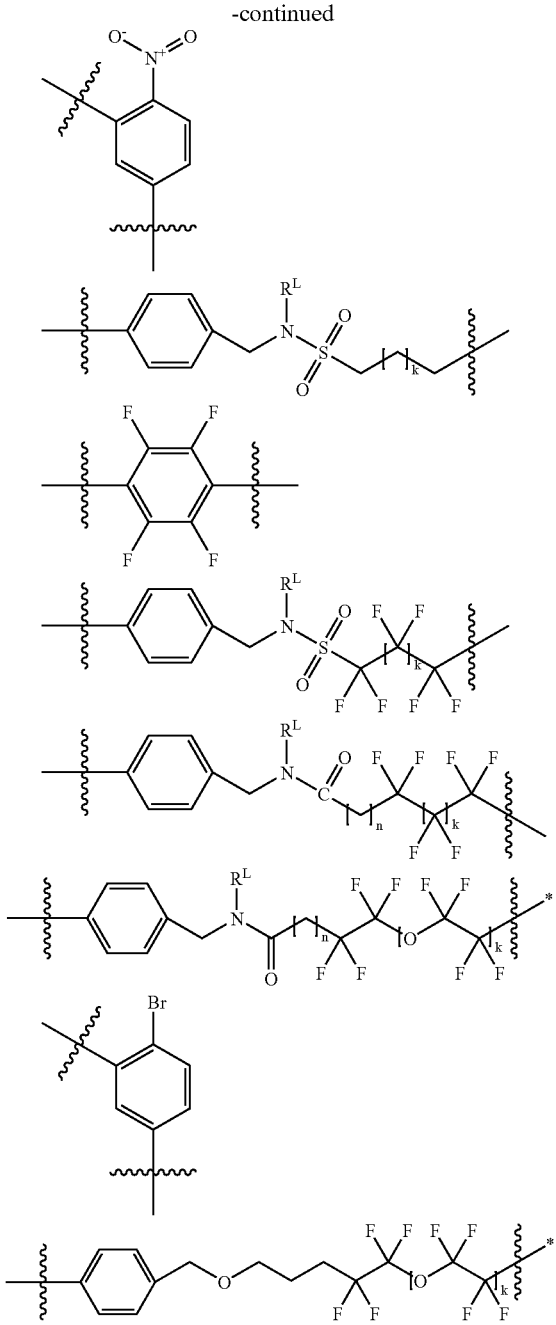

wherein at each occurrence, k is an integer of 0 to 3, n is an integer of 1 to 16, and $R^L$ is hydrogen or $C_{1-6}$ alkyl.

As would be apparent to the person skilled in the art, it may be necessary to protect functional groups in the TRACER to avoid unwanted reactions during the radiolabelling process. Such protection may be achieved using standard methods of protecting group chemistry. After the radiolabelling is complete, any protecting groups may be removed by simple procedures which are also standard in the art. Suitable protection and deprotection methodologies may be found, for example, in Protecting Groups in Organic Synthesis, Theodora W. Greene and Peter G. M. Wuts, published by John Wiley & Sons Inc. Preferred amine protecting groups include alkoxycarbonyl (such as t-butoxycarbonyl), trifluoroacetamide, fluorenylmethoxy carbonyl, and formamide. Preferred hydroxy protecting groups include alkyl or benzyl ethers, alkyloxymethyl ethers, alkoxycarbonyls (such as t-butoxycarbonyl) and silyl grups. Such protecting groups may be conveniently removed by hydrolysis, for example in the presence of acid or base. Such deprotection may be effected using a solid supported acid or base catalyst that renders the need for post deprotection neutralisation unnecessary Treatment of the compound of formula (I) or (Ia) with $^{18}F^-$ may be effected by treatment with any suitable source of $^{18}F^-$, such as $Na^{18}F$, $K^{18}F$, $Cs^{18}F$, tetraalkylammonium $^{18}F$ fluoride, or tetraalkylphosphonium $^{18}F$ fluoride. To increase the reactivity of the fluoride, a phase transfer catalyst such as 4,7,13,16,21,24 hexaoxa-1,10-diazabicyclo[8,8,8]hexacosane may be added and the reaction performed in a non protic solvent. These conditions give reactive fluoride ions. The treatment with $^{18}F^-$ is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, at a non-extreme temperature, for example, 15° C. to 180° C., preferably at elevated temperature. On completion of the reaction, the $^{18}F$-labelled tracer of formula (II) dissolved in the solvent is conveniently separated from the solid-phase by filtration. The same fluorination techniques may also be used in the following aspects of the invention.

Any excess $^{18}F^-$ may be removed from the solution of $^{18}F$-tracer by any suitable means, for example by ion-exchange chromatography or solid phase absorbents. Suitable ion-exchange resins include BIO-RAD AG 1-X8 or Waters QMA and suitable solid phase absorbents include alumina. The excess $^{18}F^-$ may be removed using such solid phases at room temperature in aprotic solvents.

Any organic solvent may be removed by any standard method such as by evaporation at elevated temperature in vacuo or by passing a stream of inert gas such as nitrogen or argon over the solution.

Before use of the $^{18}F$-labelled tracer, it may be appropriate to formulate it, for example as an aqueous solution by dissolving the $^{18}F$-labelled tracer in sterile isotonic saline which may contain up to 10% of a suitable organic solvent such as ethanol, or a suitable buffered solution such as phosphate buffer. Other additives may be added such as ascorbic acid to reduce radiolysis.

In a further aspect, the invention provides a process for the production of an $^{18}F$-labelled tracer which comprises treatment of a solid support-bound precursor of formula (Ib)

SOLID SUPPORT-LINKER-I$^+$-TRACER (Ib)
Y$^-$ wherein Y- is an anion and the TRACER is of formula (Ab)

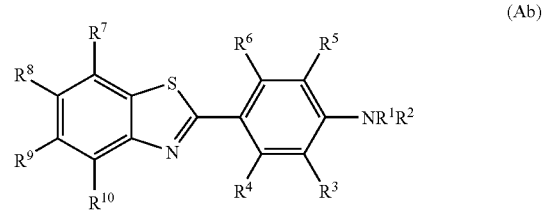

(Ab)

wherein:

$R^1$ and $R^2$ are independently selected from hydrogen, a protecting group, $C_{1-6}$ alkyl, $C_{1-6}$ hydroxyalkyl, and $C_{1-6}$ haloalkyl;

one of $R^3$ to $R^{10}$ is a bond to the SOLID SUPPORT-LINKER-$I^+$- group in formula (Ib) and the others are independently selected from hydrogen, halo, $C_{1-6}$ alkyl, $C_{1-6}$ haloalkyl, $C_{1-6}$ hydroxyalkyl, $C_{1-6}$ alkoxy, $C_{1-6}$ haloalkoxy, hydroxy, cyano, and nitro;

with $^{18}F^-$ to produce the labelled tracer of formula (IIb)

$$^{18}\text{F-TRACER} \qquad (\text{IIIb})$$

wherein the TRACER is as defined for the compound of formula (Ib) except that one of $R^3$ to $R^{10}$ is a bond to the $^{18}F$ instead of a bond to the SOLID SUPPORT-LINKER-$I^+$-group in formula (Ib);

optionally followed by:

(i) removal of excess $^{18}F^-$, for example by ion-exchange chromatography; and/or
(ii) removal of any protecting groups; and/or
(iii) removal of organic solvent; and/or
(iv) formulation of the resultant compound of formula (IIb) as an aqueous solution.

In the compound of formula (Ib), the TRACER is suitably a compound of formula (Ab1)

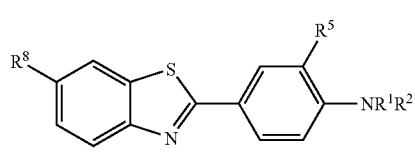

(Ab1)

wherein:

$R^1$ and $R^2$ are independently selected from hydrogen, a protecting group, $C_{1-6}$ alkyl, $C_{1-6}$ hydroxyalkyl, and $C_{1-6}$ haloalkyl;

$R^5$ is hydrogen, $C_{1-6}$ alkyl, or a bond to the SOLID SUPPORT-LINKER-$I^+$- group in formula (Ib);

$R^8$ is hydroxy, $C_{1-6}$ alkoxy, $C_{1-6}$ haloalkyl, $C_{1-6}$ alkyl, or a bond to the SOLID SUPPORT-LINKER-$I^+$- group in formula (Ib);

provided that only one of $R^5$ and $R^8$ is a bond to the SOLID SUPPORT-LINKER-I+group in formula (Ib).

The compound of formula (Ib) may be conveniently prepared from a functionalised commercially available resin such as a Merrifield Resin or Wang Resin. Suitably, a hydroxyiodoaryl (such as an iodophenol) containing LINKER group is treated with an inorganic base, such as cesium carbonate and then added to the resin, pre-swollen with an inert solvent, such as N,N-dimethylformamide and allowed to react at elevated temperature, for example 30 to 80° C. Excess reagents may be removed by washing the resin with further inert solvent. The resultant iodophenol functionalised resin may then be treated with a source of acetate anions (such as acetic acid, acetic anhydride, or acetyl chloride) in the presence of an oxidising agent, such as hydrogen peroxide to provide the corresponding diacetoxy-iodophenyl functionalised resin. The diacetoxy-iodophenyl functionalised resin may then be stirred in an inert solvent, such as dichloromethane, in the presence of acid such as hydrochloric acid, trifluoromethane sulphonic acid, or acetic acid at a low temperature, suitably −40° C. to 10° C. before addition of the tracer, suitably functionalised as a boronic acid or trialkyl tin derivative which may be coupled to the resin at a non-extreme temperature. As in previous steps, the desired compound of formula (Ib) may be separated by filtration and washing with an inert solvent.

In the compound of formula (Ib), the LINKER is as defined above but comprises an aryl group (suitably phenyl) adjacent to the $I^+$. Preferred examples include

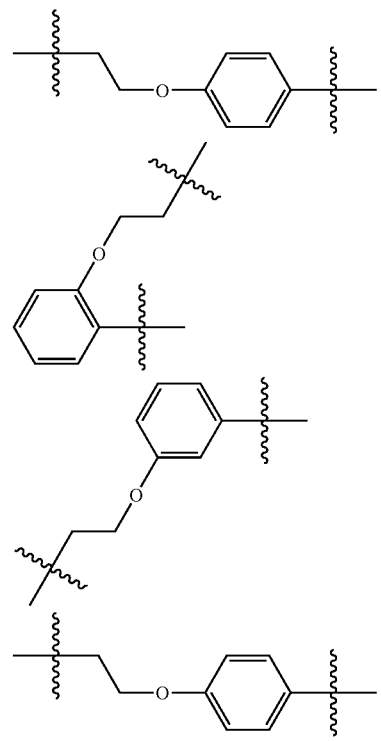

wherein each phenyl ring is optionally substituted by 1 to 4 groups selected from $C_{1-6}$-alkyl and $C_{1-6}$alkoxy, but is suitably unsubstituted.

In the compound of formula (Ib), $Y^-$ is an anion, preferably trifluoromethylsulphonate (triflate) anion or tetraphenyl borate anion.

The compounds of formula (I) are novel and thus form a further aspect of the present invention. Thus, for example, compounds of formula (Ia) and (Ib), form separate aspects of the present invention.

In an alternative aspect, the present invention provides electrophilic solid-phase processes for production of $^{18}$F-labelled benzothiazoles.

Thus in a further aspect, the present invention provides a process for the production of an $^{18}$F-labelled tracer which comprises treatment of a solid support-bound precursor of formula (III):

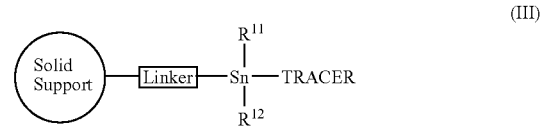

(III)

wherein $R^{11}$ and $R^{12}$ are independently selected from $C_{1-6}$ alkyl and the TRACER is a compound of formula (Ac):

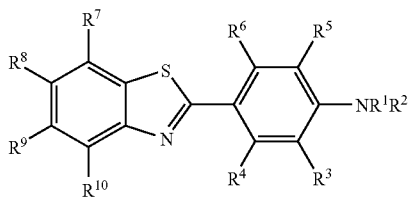

(Ac)

wherein:
$R^1$ and $R^2$ are independently selected from hydrogen, a protecting group, $C_{1-6}$ alkyl, $C_{1-6}$ hydroxyalkyl, and $C_{1-6}$ haloalkyl;
one of $R^3$ to $R^{10}$ is a bond to the Sn in formula (III) and the others are independently selected from hydrogen, halo, $C_{1-6}$ alkyl, $C_{1-6}$ haloalkyl, $C_{1-6}$ hydroxyalkyl, $C_{1-4}$ alkoxy, $C_{1-6}$ haloalkoxy, hydroxy, cyano, and nitro;
with a source of $^{18}F$, suitably $^{18}F_2$, $^{18}F$—$CH_3COOF$ or $^{18}F$—$OF_2$;
to give the labelled tracer of formula (IV);

$^{18}F$-TRACER (IV)

wherein the TRACER is as defined for the compound of formula (III) except that one of $R^3$ to $R^{10}$ is a bond to the $^{18}F$ instead of a bond to the Sn in formula (III);
optionally followed by:
(i) removal of excess fluorinating agent and $^{18}F^-$ ions produced in the generation of the fluorinating agent or in the reaction; and/or
(ii) removal of any protecting groups; and/or
(iii) removal of organic solvent; and/or
(iv) formulation of the resultant compound of formula (IV) as an aqueous solution.

In a preferred compounds of formula (III), $R^{11}$ and $R^{12}$ are both methyl.

In the compound of formula (III), the TRACER is suitably a compound of formula

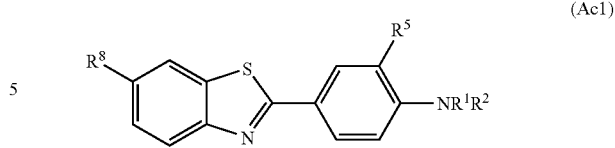

(Ac1)

wherein:
$R^{11}$ and $R^2$ are independently selected from hydrogen, a protecting group, $C_{1-6}$ alkyl, $C_{1-6}$ hydroxyalkyl, and $C_{1-6}$ haloalkyl;
$R^5$ is hydrogen, $C_{1-6}$ alkyl, or a bond to the Sn in formula (III);
$R^8$ is hydroxy, $C_{1-6}$ alkoxy, $C_{1-6}$ haloalkyl, $C_{1-6}$ alkyl, or a bond to the Sn in formula (III);
provided that only one of $R^5$ and $R^8$ is a bond to the Sn in formula (III).

Treatment of the compound of formula (III) with $^{18}F$ may be effected by treatment with any suitable source of $^{18}F$, such as $^{18}F_2$, $^{18}F$—$CH_3COOF$, or $^{18}F$—$OF_2$, in the presence of a suitable organic solvent, suitably a chlorofluorocarbon or fluorocarbon, such as trichlorofluoromethane, at a non-extreme temperature, for example, −10° C. to 60° C., preferably at ambient temperature. On completion of the reaction, the $^{18}F$-labelled tracer of formula (IV) dissolved in the solvent is conveniently separated from the solid-phase by filtration. The $^{18}F_2$ may be produced, for example, by the $20Ne(d,\alpha)$ $^{18}F$ reaction using the 13.5 Mev deuterons of the Rossendorf cyclotron U-120 with Ne+0.2% $F_2$ (100 umol) as target gas. Alternatively, the $^{18}F_2$ may be produced by the $^{18}O_2(p,n)$ $^{18}F$ reaction, using 11Mev protons from a cyclotron (A. J. Bishop et al, J. Nucl. Med., 32:1010(1991)).

After reaction of the compound of formula (III), any excess fluorinating agent or $^{18}F$ ions produced in the generation of the fluorinating agent or in the reaction and may be removed from the solution of $^{18}F$-tracer of formula (IV) by any suitable means, for example by passing through a column of sodium sulphite and silica gel in a suitable solvent, suitably a chlorofluorocarbon or a chlorocarbon, such as chlorofluoromethane or methylene chloride.

Compounds of formula (III) may be prepared from commercially available starting materials as outlined in Scheme 2 or Scheme 3.

Scheme 2

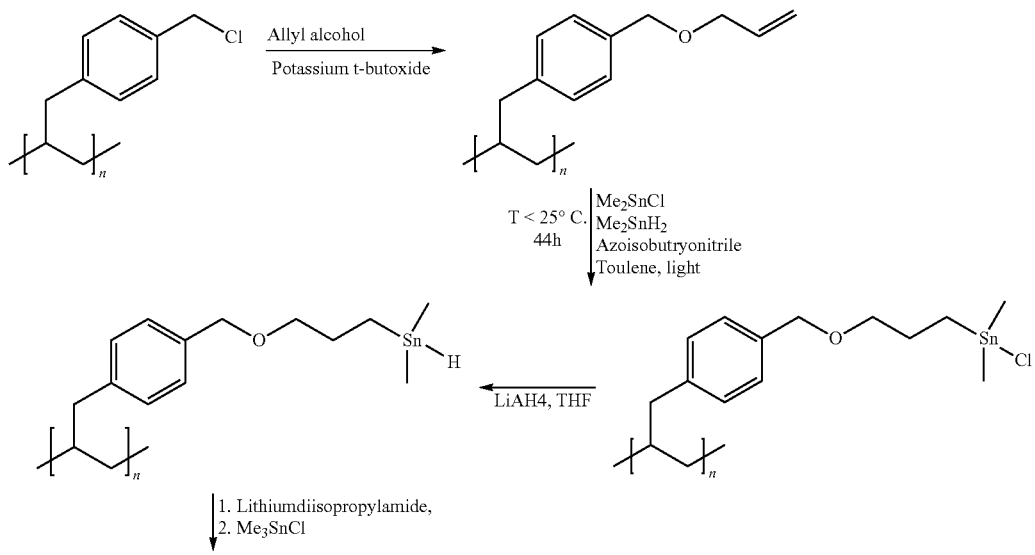

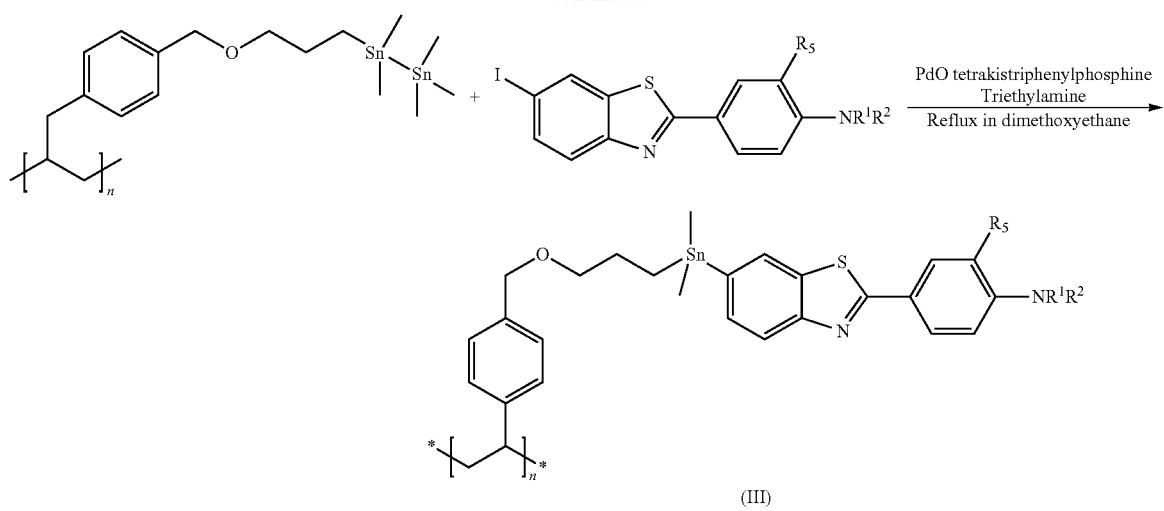
(III)
Scheme 3
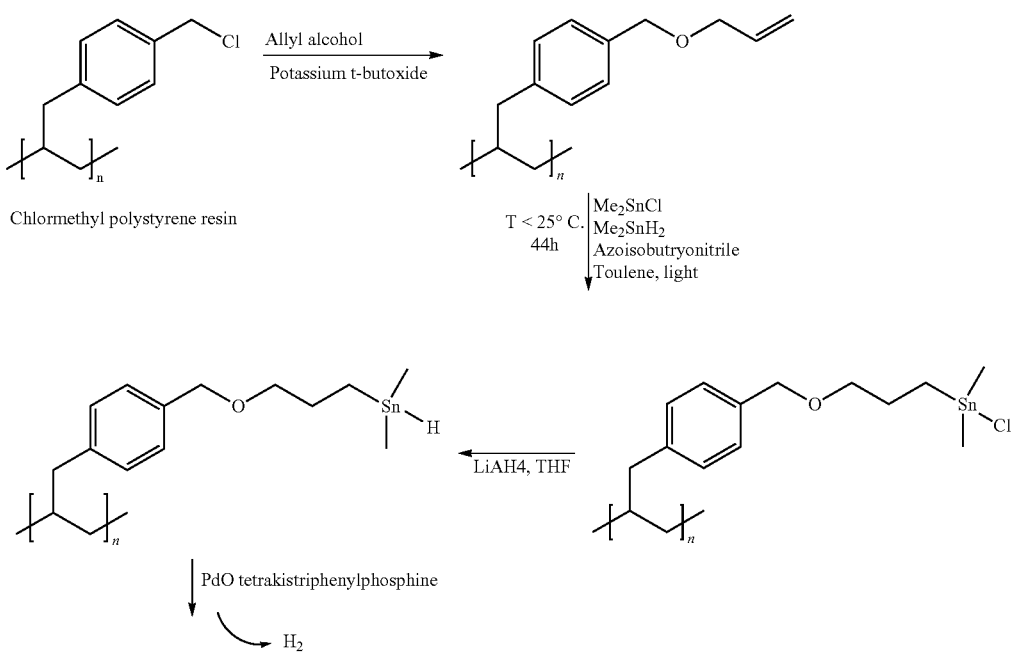
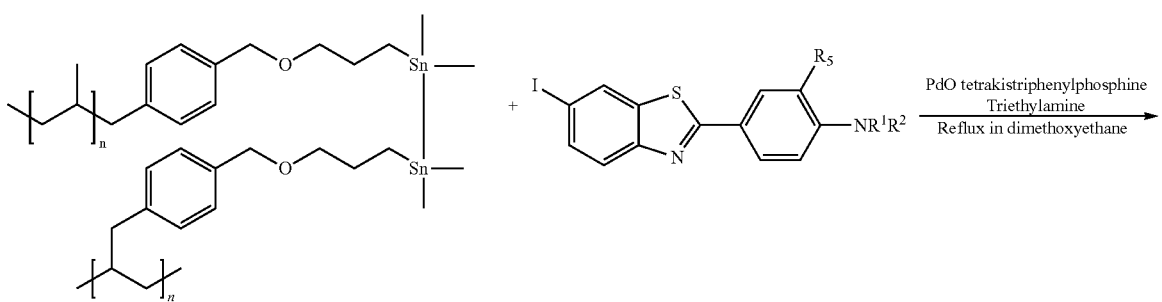

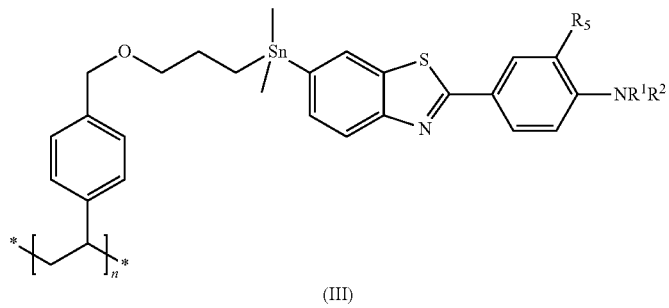

(III)

As described above, the advantages of such solid-phase processes for preparation of $^{18}$F-labelled tracers include the relative speed of the process, simplified purification methods and ease of automation—all of which mean that the processes are suitable for preparation of $^{18}$F-labelled tracers for use in PET. Accordingly, the present invention provides a process for the preparation of a $^{18}$F-labelled tracer of formula (II), (IIa), (IIb), or (IV) for use in PET.

Conveniently, the solid support bound precursor of formula (I) or (III) could be provided as part of a kit to a radiopharmacy. The kit may contain a cartridge which can be plugged into a suitably adapted automated synthesiser. The cartridge may contain, apart from the solid support-bound precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers requirements for radioactive concentration, volumes, time of delivery etc.

Conveniently, all components of the kit are disposable to minimise the possibilities of contamination between runs and may be sterile and quality assured.

The invention further provides a radiopharmaceutical kit for the preparation of an $^{18}$F-labelled tracer for use in PET, which comprises:
(i) a vessel containing a compound of formula (I), (Ia), or (Ib) as defined above; and
(ii) means for eluting the vessel with a source of $^{18}$F$^-$;

(iii) an ion-exchange cartridge for removal of excess $^{18}$F$^-$; and optionally
(iv) a cartridge for solid-phase deprotection of the resultant product of formula (II), (IIa), or (IIb) as defined above.

The invention further provides a cartridge for a radiopharmaceutical kit for the preparation of an $^{18}$F-labelled tracer for use in PET which comprises:
(i) a vessel containing a compound of formula (I), (Ia), or (Ib); and
(ii) means for eluting the vessel with a source of $^{18}$F$^-$.

The invention further provides a radiopharmaceutical kit for the preparation of of an $^{18}$F-labelled tracer for use in PET, which comprises:
(i) a vessel containing a compound of formula (III) as defined above; and
(ii) means for eluting the vessel with a source of $^{18}$F; and optionally
(iii) a cartridge for removal of excess fluorinating agent and $^{18}$F$^-$ ions; and optionally
(iv) a cartridge for solid-phase deprotection of the resultant product of formula (IV) as defined above.

The invention further provides a cartridge for a radiopharmaceutical kit for the preparation of an $^{18}$F-labelled tracer for use in PET which comprises:
(i) a vessel containing a compound of formula (III) as defined above; and
(ii) means for eluting the vessel with a source of $^{18}$F.

In a further aspect of the invention, there is provided a method for obtaining a diagnostic PET image which comprises the step of using a radiopharmaceutical kit or a cartridge for a radiopharmaceutical kit as described above.

The invention is illustrated by way of the following Examples:

EXAMPLE 1

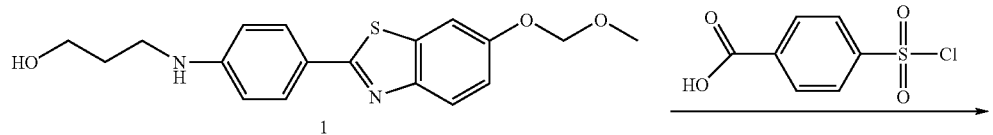

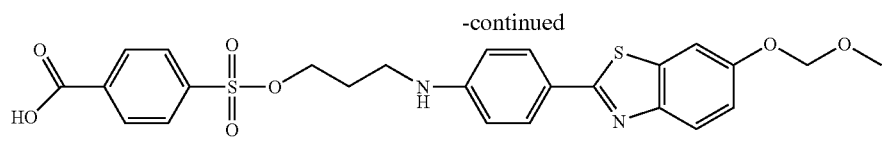

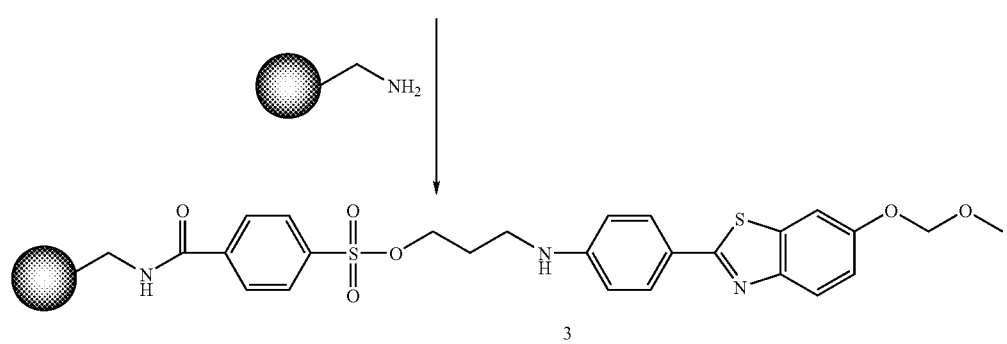

6-Methoxymethoxy-2-(phenyl-4'-aminopropanol)-benzothiazole 1 is dissolved in pyridine/DCM (1:1) in presence of 4-(chlorosulfonyl)benzoic acid (1eq). The reaction is stirred at room temperature for 12 hours. After an aqueous work-up, compound 2 is purified on silica gel.

In an oven-dried Radleys reaction tube is placed 1 g of polystyrene resin (1 g, 1.30 mmol.g$^{-1}$, Novabiochem 01-64-0143, 100-200 mesh) and 16 mL of dry DCM (Aldrich). To this is added sequentially compound 2 (1.1 equivalent), Hunig's base (2.0 equivalent) and DPPCI (1.1 equivalent). After 5 hours the resin is filtered of and washed thoroughly with DCM and methanol. The solid is dried at reduced pressure.

EXAMPLE 2

Radiofluorination to Prepare [$^{18}$F]-Benzothiazole Tracer

To a portion of the resin (prepared as described in Example 1 compound 3) held in a cartridge is added a solution in dry acetonitrile of kryptofix, potassium carbonate and [$^{18}$F]-fluoride. The suspension is heated to 85° C. for 10 minutes and then the solution is filtered off. The solution is diluted with water, passed onto a C$_{18}$ solid phase extraction cartridge and washed with water to remove acetonitrile, kryptofix, potassium carbonate and unreacted [$^{18}$F]fluoride. The radiofluorinated product is eluted from the cartridge with organic solvent and the protecting groups are removed by heating in an acidic solution before neutralization and analysis.

The invention claimed is:
1. A process for the production of an $^{18}$F-labelled tracer which comprises treatment of a solid support-bound precursor of formula (Ib)

SOLID SUPPORT-LINKER-I$^+$-TRACER

Y$^-$    (Ib)

wherein Y$^-$ is an anion, the SOLID SUPPORT is a polymer selected from polystyrene which is optionally block grafted, polyacrylamide, and polypropylene or glass or silicon coated with such a polymer, the LINKER is selected from:

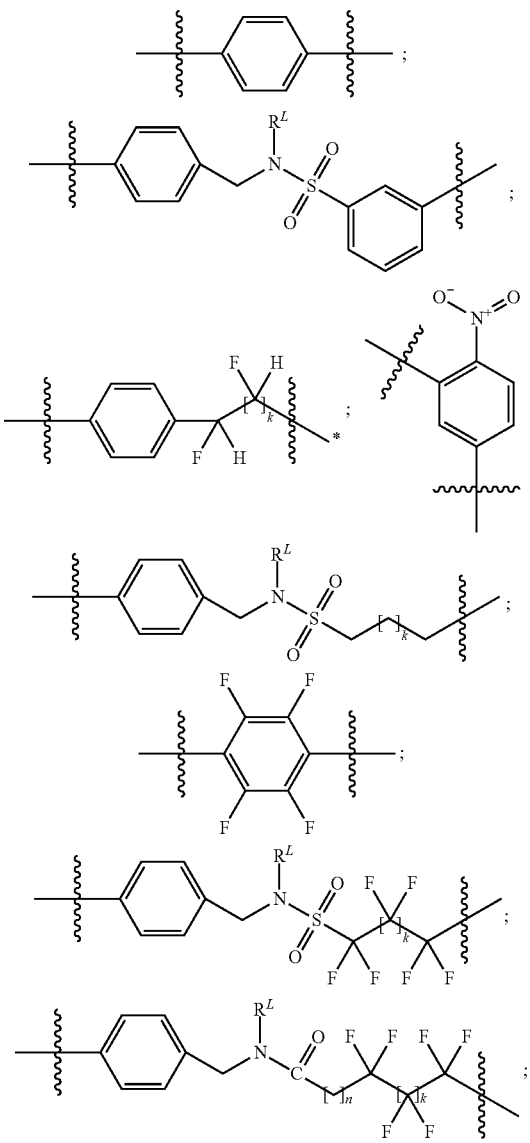

-continued

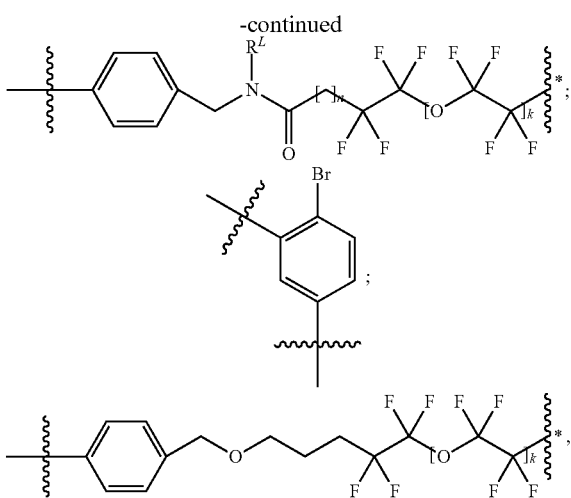

wherein at each occurrence, k is an integer of 0 to 3, n is an integer of 1 to 16, and $R^L$ is hydrogen or C1-6alkyl; and

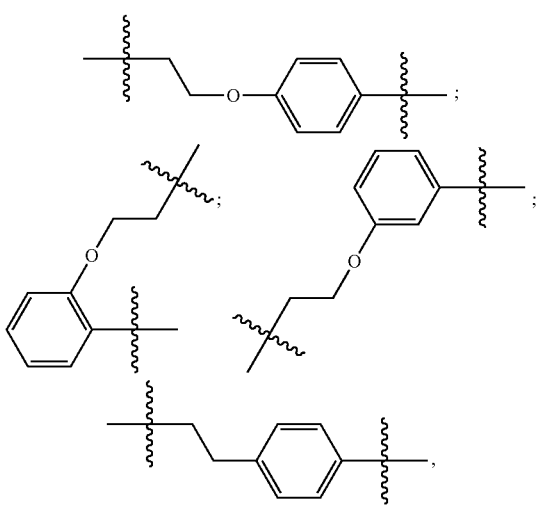

wherein each phenyl ring is optionally substituted by 1 to 4 groups selected from $C_{1-6}$alkyl and $C_{1-6}$alkoxy; and the TRACER is of formula (Ab1)

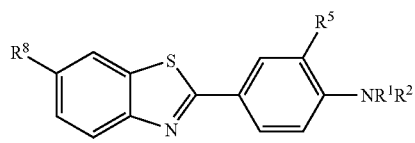
(Ab1)

wherein:
$R^1$ and $R^2$ are independently selected from hydrogen, $C_{1-6}$ alkyl, $C_{1-6}$ hydroxyalkyl, $C_{1-6}$haloalkyl, and a protecting group selected from alkoxycarbonyl;

$R^5$ is hydrogen, $C_{1-6}$ alkyl, or a bond to the SOLID SUPPORT-LINKER-$I^+$- group in formula (Ib);

$R^8$ is hydroxy, $C_{1-6}$ alkoxy, $C_{1-6}$ haloalkyl, $C_{1-6}$ alkyl, or a bond to the SOLID SUPPORT-LINKER-$I^+$- group in formula (Ib);

provided that only one of $R^5$ and $R^8$ is a bond to the SOLID SUPPORT-LINKER-$I^+$- group in formula (Ib);

with $^{18}F$ to produce the labelled tracer of formula (IIb)

$^{18}$F-TRACER (IIb)

wherein the TRACER is as defined for the compound of formula (Ib) except that one of $R^5$ and $R^8$ is a bond to the $^{18}F$ instead of a bond to the SOLID SUPPORT-LINKER-$I^+$- group in formula (Ib);

optionally followed by:
(i) removal of excess $^{18}F^-$; and/or
(ii) removal of any protecting groups; and/or
(iii) removal of organic solvent; and/or
(iv) formulation of the resultant compound of formula (IIb) as an aqueous solution.

2. A process according to claim 1 wherein the LINKER is selected from:

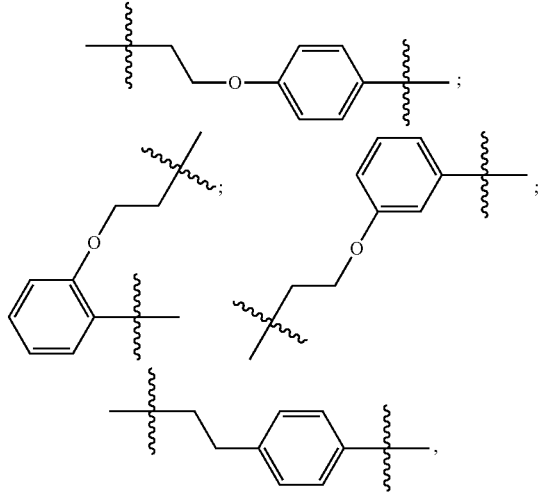

wherein each phenyl ring is optionally substituted by 1 to 4 groups selected from $C_{1-6}$alkyl and $C_{1-6}$alkoxy.

* * * * *